(12) United States Patent
Kanai et al.

(10) Patent No.: US 12,357,579 B2
(45) Date of Patent: Jul. 15, 2025

(54) CAPSULE FOR TREATING ULCERATIVE COLITIS

(71) Applicants: KEIO UNIVERSITY, Tokyo (JP); Foundation for Biomedical Research and Innovation at Kobe, Kobe (JP); MORISHITA JINTAN CO., LTD., Osaka (JP)

(72) Inventors: Takanori Kanai, Tokyo (JP); Hideo Nishimura, Kobe (JP); Tomoyuki Koyama, Hirakata (JP); Takuhiko Adachi, Hirakata (JP); Hiroyuki Hayakawa, Hirakata (JP)

(73) Assignees: KEIO UNIVERSITY, Tokyo (JP); FOUNDATION FOR BIOMEDICAL RESEARCH AND INNOVATION AT KOBE, Kobe (JP); MORISHITA JINTAN CO., LTD., Osaka (JP)

( * ) Notice: Subject to any disclaimer, the term of this patent is extended or adjusted under 35 U.S.C. 154(b) by 0 days.

(21) Appl. No.: 18/310,999

(22) Filed: May 2, 2023

(65) Prior Publication Data

US 2023/0263740 A1    Aug. 24, 2023

Related U.S. Application Data (62) Division of application No. 16/962,968, filed as application No. PCT/JP2019/001002 on Jan. 16, 2019, now abandoned.

(30) Foreign Application Priority Data

Jan. 18, 2018 (JP) .................. 2018-006659

(51) Int. Cl.
  *A61K 9/48* (2006.01)
  *A61K 31/404* (2006.01)
  *A61P 1/04* (2006.01)

(52) U.S. Cl.
  CPC .......... *A61K 9/4891* (2013.01); *A61K 9/4866* (2013.01); *A61K 9/4875* (2013.01); *A61K 31/404* (2013.01); *A61P 1/04* (2018.01)

(58) Field of Classification Search
  None
  See application file for complete search history.

(56) References Cited

U.S. PATENT DOCUMENTS

| | | | |
|---|---|---|---|
| 7,354,570 B2 | 4/2008 | Wang et al. | |
| 8,476,233 B2* | 7/2013 | Pravda | A61K 9/0031 514/435 |
| 9,107,819 B2 | 8/2015 | Haeusler et al. | |
| 2005/0154046 A1* | 7/2005 | Wang | A61P 35/00 514/414 |
| 2013/0259933 A1* | 10/2013 | Kamaguchi | A61K 35/747 264/4.4 |
| 2018/0055776 A1* | 3/2018 | Draper | A61P 3/02 |
| 2019/0105278 A1 | 4/2019 | Wätzig et al. | |

FOREIGN PATENT DOCUMENTS

| | | |
|---|---|---|
| CN | 1660357 | 8/2005 |
| CN | 100512834 C | 7/2009 |
| JP | 2987576 | 10/1999 |
| JP | 5102401 | 10/2012 |
| JP | 2013-209297 | 10/2013 |
| JP | 5383977 | 10/2013 |
| WO | 2014/097664 | 6/2014 |
| WO | 2017/182350 | 10/2017 |

OTHER PUBLICATIONS

Tahan et al (Can J Surg, Oct. 2011, 54(5): 333-338) (Year: 2011).*
Biopharmaceutics, edited by Cheng Gang, Beijing: China Medical Science and Technology Press, 1st printing, Sep. 2010, p. 67; with English translation.
Office Action issued for Chinese Patent Application No. 201980020526. 7, May 18, 2023, 23 pages with English translation.
Office Action issued for Korean Patent Application No. 10-2020-7023524, Jun. 25, 2023, 6 pages with machine translation.
Naganuma, Makoto et al., "Efficacy of Indigo naturalis in a Multicenter Randomized Controlled Trial of Patients with Ulcerative Colitis", Gastroenterology, published online on Nov. 22, 2017, 154, 935-947.
PSEHB/CND Notification No. 1227-9, Dec. 27, 2016, 3 pages (See paragraph [0004] of the Specification for a concise explanation.).
Sugimoto, Shinya et al., "Indole compounds may be promising medicines for ulcerative colitis," J. Gastroenterol. vol. 51, 853-861 (2016).
Kawai, Shoichiro et al., "Indigo Naturalis ameliorates murine dextran sodium sulfate-induced colitis via aryl hydrocarbon receptor activation," J. Gastroenterology vol. 52, 904-919 (2017).
Hayashi, Shusaku, "Is Indigo-Containing Deep Blue [Seitai] a Novel Treatment for Ulcerative Colitis, " Farumashia, vol. 53, No. 8, 820 (2017) (A concise explanation of relevance provided in the International Search Report submitted herewith.).
International Search Report of PCT/JP2019/001002, Mar. 12, 2019, 4 pages including English translation.
International Preliminary Report on Patentablity of PCT/JP2019/001002, Jul. 21, 2020, 9 pages.

(Continued)

*Primary Examiner* — Celeste A Roney
(74) *Attorney, Agent, or Firm* — HSML P.C.

(57) ABSTRACT

An object of the present invention is to obtain a capsule for treating ulcerative colitis which, when a capsule containing indigo is orally administered, acts more effectively than conventional ones and has less side effects of hepatotoxicity by not easily disintegrating in the stomach and small intestine but only in the large intestine. The present invention relates to a capsule for treating ulcerative colitis which disintegrates locally in the large intestine, comprising a drug-containing content, a protective layer coating the content and a film formed outside the protective layer, which are arranged concentrically, wherein the content is a content in which indigo, which is a drug for treating ulcerative colitis, is dispersed or dissolved, and the film is locally disintegrated in the large intestine.

12 Claims, 3 Drawing Sheets

(56) References Cited

OTHER PUBLICATIONS

The extended European search report issued for European Patent Application No. 19741610.0, Nov. 22, 2021, 7 pages.
Sato, Kiyohito et al., "Dietary Supplementation of Catechnis and .ALPHA.-Tocopherol Accelerates the Healing of Trinitrobenzene Sulfonic Acid-Induced Ulcerative Colitis in Rats," J Nutr Sci Vitaminol, 1998, vol. 44, pp. 769 to 778.
Office Action issued for Japanese Patent Application No. 2019-566477, Jul. 12, 2022, 6 pages including machine translation.
Pharmacy/Edited by Lu Bin—Beijing: China Medical Science and Technology Press, Jan. 2003, pp. 421-422; English translation provided.
Office Action issued for Chinese Patent Application No. 201980020526.7, Nov. 3, 2022, 12 pages including English translation.

* cited by examiner

CAPSULE FOR TREATING ULCERATIVE COLITIS

TECHNICAL FIELD

The present invention is related to a capsule for treating ulcerative colitis, specifically, a capsule for treating ulcerative colitis that does not easily disintegrate in the stomach and small intestine when orally administered, and disintegrates in the large intestine so that indigo is delivered directly to the large intestine and the capsules are a specific therapeutic formulation for ulcerative colitis.

BACKGROUND ART

Qing-Dai (青黛) is a crude component extracted from plants containing indigo, and has been mainly used as an indigo dye. Chinese herbal medicines containing Qing-Dai have been used for ulcerative colitis for a long time in China, but they have not been sufficiently scientifically verified.

In Gastroenterology: "Efficacy of Indigo naturalis in a Multicenter Randomized Controlled Trial of Patients with Ulcerative Colitis", Makoto Naganuma et al., published online on Nov. 22, 2017 (Non Patent Literature 1), in order to scientifically prove effectiveness of Qing-Dai against ulcerative colitis, a double-blind dose-response comparative trial, that compared oral administration of Qing-Dai in three groups with daily doses of 0.5 g, 1.0 g and 2.0 g and placebo in 86 patients with ulcerative colitis, was conducted. Its result indicates that the oral administration of Qing-Dai showed significant improvement in all doses and evaluation indexes when comparing to the placebo group. In this trial, it was shown that Qing-Dai would be expected to have excellent therapeutic effects on ulcerative colitis, which was intractable and whose patient's quality of life (QOL) was extremely poor.

However, the Ministry of Health, Labor and Welfare notified that "in patients with ulcerative colitis who used Qing-Dai, it was found that there were a plurality of patients that exhibit pulmonary arterial hypertension," (PSEHB/CND Notification No. 1227-9, Dec. 27, 2016 (Non Patent Literature 2)).

Pulmonary arterial hypertension is one of serious adverse effects. Therefore, instead of administration of Qing-Dai itself, a formulation to be delivered to the large intestine while suppressing the dose by a pure medicinal active ingredient without impurities is required.

JP 2987576 B1 (Patent Literature 1) discloses a medicinal composition which comprises an extract of Indigofera arrecta for treating gastric ulcer and duodenal ulcer which are peptic ulcers. In examples of Patent Literature 1, the extract of Indigofera arrecta is enclosed in a capsule and administered to mice, and it is shown to be effective for peptic ulcer. However, what is used in this literature is an extract of Indigofera arrecta, not indigo itself, and the capsule used in this technique is a normal capsule used for oral administration to humans.

On the other hand, indigo, which is the main medicinal active ingredient of Qing-Dai, is an indole compound, and the indole compound has recently attracted attention as a substance that promotes mucosal healing. JP 5383977 B1 (Patent Literature 2) discloses a pharmaceutical composition for treating and/or preventing Crohn's disease or ulcerative colitis containing indigo compounds such as indigo and isoindigo (particularly, meisoindigo). It is also described that the pharmaceutical compositions take the form of capsules (see claim 1 and paragraphs [0045] to [0048] of Patent Literature 2). It is, however, merely mentioned as a capsule in Patent Literature 2 and its form is not explained at all. Administration in a capsule is not described in the examples of Patent Literature 2. Those used in the examples of Patent Literature 2 are pellets of meisoindigo.

Patent Literature 3 describes a large intestine disintegrating capsule. However, the content of the capsule described in Patent Literature 3 is mainly lactic acid bacteria and water-soluble proteinaceous molecules, and are described to be used for the purpose of preventing deterioration of quality due to pH and degrading enzymes. On the other hand, the capsule for treating ulcerative colitis of the present invention has a problem that the drug acts only on the large intestine to be treated. However, in this present invention, the content is indigo, which is a molecule having extremely poor solubility in water and oil. It cannot be expected only from the description in Patent Literature 3 that indigo is actually administered to a living body and held without disintegrating in the stomach and small intestine, and disintegrates only in the large intestine to act, and effects can be seen only in the large intestine. Therefore, the present invention cannot be easily completed by a person skilled in the art from the description in Patent Literature 3.

J. Gastroenterol. Vol. 51, 853-861 (2016) (Non Patent Literature 3) describes that indole compounds including indigo are therapeutic drug candidates for ulcerative colitis, and the effect thereof is mediated by an aryl hydrocarbon receptor (AhR) which is one of mechanisms involved in mucosal healing. Furthermore, J. Gastroenterology Vol. 52, 904-919 (2017) (Non Patent Literature 4) describes that a mouse model of colitis had a therapeutic effect by administering Indigo naturaris (IN) powder or indigo powder, and that the action of IN and indigo occurs via binding to an aryl hydrocarbon receptor (AhR) in a local mucous membrane (p. 914, right column, lines 30 to 32 of Non Patent Literature 4). On the other hand, the aryl hydrocarbon receptor (AhR) is also present in the small intestine, and from the description of these literatures, it is expected that when an indole compound such as IN, indigo or isoindigo comes into contact with the small intestine, it is absorbed through the aryl hydrocarbon receptor (AhR) in the small intestine, and the side effects as described in Non Patent Literature 2 may occur.

Therefore, when a formulation containing an indole compound such as indigo is developed, contact with the small intestine as described in the above literatures may increase absorption in the small intestine, which may trigger an onset of pulmonary arterial hypertension. Thus, a formulation to be delivered only to the large intestine is desired, in which, when a formulation containing indigo is orally administered, it does not disintegrate in the stomach and small intestine so that the indigo compound does not come into contact with the small intestine, and disintegrates and exerts its effect only after being delivered to the large intestine.

CITATIONS LIST

Patent Literature

Patent Literature 1: JP 2987576 B1
Patent Literature 2: JP 5383977 B1
Patent Literature 3: JP 5102401 B1

Non-Patent Literature

Non Patent Literature 1: Gastroenterology: Inpress "Efficacy of Indigo naturalis in a Multicenter Randomized Controlled Trial of Patients with Ulcerative Colitis", Makoto Naganuma et al., published online on Nov. 22, 2017.

Non Patent Literature 2: PSEHB/CND Notification No. 1227-9, Dec. 27, 2016

Non Patent Literature 3: J. Gastroenterol. Vol. 51, 853-861 (2016)

Non Patent Literature 4: J. Gastroenterology Vol. 52, 904-919 (2017)

SUMMARY OF INVENTION

Technical Problems

An object of the present invention is to obtain a capsule for achieving less side effects and more effective action on ulcerative colitis than conventional ones, in capsule technique, when the capsule including indigo is orally administered to a patient having a disease of enteritis or the like.

Solutions to Problems

As a result of repeated intensive research to solve the above objects, the present inventors have found that when indigo is orally administered to model animals induced colitis by sodium dextran sulfate in the form of a capsule (capsule that does not easily disintegrate in the stomach and small intestine and disintegrates in the large intestine), it functions more effectively on ulcerative colitis without causing hepatotoxicity (one of the side effects due to contact/absorption in the small intestine), and they have achieved the present invention. That is, the present invention provides a capsule for treating ulcerative colitis which disintegrates locally in the large intestine, which comprises a drug-containing content, a protective layer coating the content and a film formed outside the protective layer exist, which are arranged concentrically, wherein the content is a content in which indigo, which is an active ingredient for treating ulcerative colitis, is dispersed or dissolved, the protective layer contains an oily substance, the film is a film which chitosan powder is dispersed in a film base material of a natural water-soluble polymer, and the natural water-soluble polymer is a mixture of a first natural water-soluble polymer and a second natural water-soluble polymer, the first natural water-soluble polymer is composed of one or a mixture of at least two selected from the group consisting of gelatin, carrageenan, starch, agar, pullulan, modified starch, alginic acid and mannan, and the second natural water-soluble polymer is composed of one or a mixture of at least two selected from the group consisting of pectin, gellan gum and curdlan.

The film preferably further contains a plasticizer.

It is preferred that the chitosan powder is of animal or plant origin, and amount of the chitosan powder falls within the range of 1 to 27% by mass, and amount of the second natural water-soluble polymer falls within the range of 1 to 24% by mass, based on the total weight of the dried film.

The film base material of the natural water-soluble polymer is preferably a mixture of gelatin and pectin.

One selected from the group consisting of the content, the protective layer and the film or a combination selected from the group consisting of the content, the protective layer and the film, of the capsule for treating ulcerative colitis, more preferably contains an adherable substance to an epithelial of large intestine, a substance increasing residence time in the large intestine or a combination thereof.

An adherable substance to an epithelial of large intestine, a substance increasing residence time in the large intestine or a combination thereof may be allowed to be present on the outer surface of the film of the capsule for treating ulcerative colitis.

The capsule for treating ulcerative colitis may comprise the content which contains indigo powder and an adherable substance to an epithelial of large intestine, and the indigo powder may be blended or coated with an adherable substance to an epithelial of large intestine.

The capsule for treating ulcerative colitis is preferably for oral administration.

It is preferred that the capsule for treating ulcerative colitis is administered in amount of indigo per adult (60 kg) of 0.05 to 120 mg/day, and preferably 0.05 to 20 mg/day.

In another embodiment of the present invention, (1) a capsule for treating ulcerative colitis, which disintegrates locally in the large intestine, including a drug-containing content, a protective layer coating the content and a film formed outside the protective layer, which are arranged concentrically, wherein the content is a content in which indigo which is a drug for treating ulcerative colitis, is dispersed or dissolved, the protective layer contains an oily substance, the film is a film which chitosan powder is dispersed in a film base material of a natural water-soluble polymer, and the natural water-soluble polymer is a mixture of a first natural water-soluble polymer and a second natural water-soluble polymer, the first natural water-soluble polymer is composed of one or a mixture of at least two selected from the group consisting of gelatin, carrageenan, starch, agar, pullulan, modified starch, alginic acid and mannan, and the second natural water-soluble polymer is composed of one or a mixture of at least two selected from the group consisting of pectin, gellan gum and curdlan, (2) the capsule for treating ulcerative colitis according to (1) above, in which the film further contains a plasticizer, (3) the capsule for treating ulcerative colitis according to (1) or (2) above, in which the chitosan powder is of animal origin or plant origin, and amount of the chitosan powder falls within the range of 1 to 27% by mass, and amount of the second natural water-soluble polymer falls within the range of 1 to 24% by mass, based on the total weight of the dried film, (4) the capsule for treating ulcerative colitis according to any one of (1) to (3) above, in which the film base material of the natural water-soluble polymer is a mixture of gelatin and pectin, (5) the capsule for treating ulcerative colitis according to (1) to (4) above, which has been treated with an acidic solution in advance, (6) the capsule for treating ulcerative colitis according to any one of (1) to (5) above, in which one selected from the group consisting of the content, the protective layer and the film or a combination thereof further contains an adherable substance to an epithelial of large intestine, a substance increasing residence time in the large intestine or a combination thereof, (7) the capsule for treating ulcerative colitis according to any one of (1) to (5) above, in which an adherable substance to an epithelial of large intestine, a substance increasing residence time in the large intestine or a combination thereof is allowed to be present on the outer surface of the film, (8) the capsule for treating ulcerative colitis according to any one of (1) to (5) above, including the content which contains indigo powder and an adherable substance to an epithelial of large intestine, wherein the indigo powder is blended or coated with the adherable substance to the epithelial of large intestine, (9) the capsule for treating ulcerative colitis according to any one of (1) to (8) above, which is for oral administration, (10) the capsule for treating ulcerative colitis according to any one of (1) to (9) above, which is administered in amount of indigo per adult (60 kg) of 0.05 to 120 mg/day, and (11) the capsule for treating ulcerative colitis according to (1) to (9) above, which is administered in amount of indigo per adult (60 kg) of 0.05 to 20 mg/day.

Advantageous Effects of Invention

According to the present invention, indigo which is a drug for treating ulcerative colitis is coated with a large intestine disintegrating capsule, so that it suppresses disintegration in the stomach and small intestine, and without being contacted to or absorbed in the stomach or small intestine, reaches the large intestine and disintegrates, and the drug acts. Therefore, since indigo reaches the large intestine at a high concentration without being dispersed in the upper gastrointestinal tract such as the stomach and small intestine, its effect is locally exerted in the large intestine, and further, there is few concern of side effects due to contact and absorption in the stomach and small intestine. The effectiveness of the capsule for treating ulcerative colitis of the present invention has been confirmed in mouse experiments.

Qing-Dai has been known to be effective against ulcerative colitis as a Chinese herbal medicine for a long time, and its main active ingredient, indigo, is not dispersed in upper gastrointestinal tracts (stomach and small intestine) and directly reaches the large intestine, whereby an excellent effect of Qing-Dai has been confirmed. Although severe pulmonary arterial hypertension and the like have been reported as side effects of indigo, these can be also expected to be alleviated.

In addition, when an adherable substance to an epithelial of large intestine, a substance increasing residence time in the large intestine or a combination thereof is contained, in any part(s) of the capsule of the present invention, for example, the inside of the content, the protective layer, the film or a combination thereof, or in the form of a coating on the outside of the film, the contact time of indigo in the large intestine is increased, and a greater therapeutic effect on ulcerative colitis is expected.

DESCRIPTION OF EMBODIMENTS

The capsule for treating ulcerative colitis which disintegrates locally in the large intestine of the present invention is a capsule in which a content containing indigo being an active ingredient for treating ulcerative colitis, a protective layer coating the content and a film formed outside the protective layer, which are arranged concentrically. The content of the capsule will be described first.

The content of the capsule for treating ulcerative colitis of the present invention is a content in which indigo which is a drug for treating ulcerative colitis is dispersed or dissolved. Indigo is a compound having the following chemical formula:

[Chemical Formula 1]

and is also used as a dye showing indigo color. Indigo is a pigment component of indigo and has been extracted from plants (*Strobilanthes cusia, Persicaria tinctoria*) and the like, but is currently synthesized from aniline. Qing-Dai is a crude component containing indigo, and although it may be used as the content of the present invention, a synthetic product (indigo) is preferably used, because it has a purity of 95% or more and controls side effects.

The content of the capsule for treating ulcerative colitis of the present invention contains indigo which is a drug for treating ulcerative colitis as described above, and indigo is suspended in an oily substance. The reason for suspending in an oily substance in this way is that the content is not affected by a large amount of water and the like that are present during capsule production. The oily substance is non-fluid at room temperature, and examples thereof include edible hardened oil and fat, sucrose fatty acid ester (SAIB), glycerin fatty acid ester and the like, and mixtures thereof. A particularly preferable oily substance is glycerin fatty acid ester, and examples thereof include glycerin fatty acid ester with a melting point of 32° C. or 42° C.

In the capsule for treating ulcerative colitis of the present invention, the amount of the drug (that is, indigo) in the above content usually falls within the range of 0.1 to 40% by mass, preferably 0.5 to 30% by mass, and more preferably 1 to 20% by mass. When it is more than 40% by mass, encapsulation becomes difficult, and when it is less than 0.1% by mass, it becomes difficult to secure a desired dose. The amount of indigo per capsule preferably falls within the range of 0.1 mg/cap to 20 mg/cap, more preferably 0.1 mg/cap to 10 mg/cap, and further preferably 0.1 mg/cap to 5 mg/cap. The content of the capsule for treating ulcerative colitis of the present invention may appropriately contain pharmaceutically acceptable excipients, stabilizers, surfactants, adjuvants, foaming agents, or the like. The amount of the additive agents is not particularly limited, but should not be amount that inhibits an action of the capsule for treating ulcerative colitis of the present invention.

In the capsule for treating ulcerative colitis of the present invention, the content is generally covered with two layers (the protective layer and the film). The method of encapsulation is not particularly limited, but the most preferable method includes a method of dropping into a coagulating liquid using a triple nozzle generally called a dropping method (for example, JP 49-59789 A, JP 51-8176 A and JP 60-172343 A).

In the three-layer structure capsule of the present invention, a protective layer is formed on a surface of the content. The protective layer contains an oily substance. The oily substance is the same as that is formulated in the above content, but it is preferable to use an oily substance having a melting point 2 to 9° C. higher and preferably 2 to 8° C. higher than the melting point of the content, so that hardening (or curing) can be controlled during cooling in the capsule forming process. When the difference in melting point is less than 2° C., the content and the protective layer would be mixed during cooling, and on the contrary, when the difference in melting point is higher than 9° C., the protective layer does not solidify, thereby hindering capsule formation. Lecithin and silicon dioxide can be blended in the protective layer in order to adjust interfacial tension, viscosity or specific gravity.

The protective layer is further coated with a film. The film is a film which chitosan powder is dispersed in a film base material of a natural water-soluble polymer, and the natural water-soluble polymer is a mixture of a first natural water-soluble polymer and a second natural water-soluble polymer, the first natural water-soluble polymer is composed of one or a mixture of at least two selected from the group consisting of gelatin, carrageenan, starch, agar, pullulan, modified starch, alginic acid and mannan, and the second natural water-soluble polymer is composed of one or a mixture of at least two selected from the group consisting of pectin, gellan gum and curdlan.

The natural water-soluble polymer used in the film base material of the capsule of the present invention is preferably a combination of a first natural water-soluble polymer that imparts excellent mechanical strength and film-forming ability and adhesiveness to a capsule to be obtained, and a second natural water-soluble polymer that imparts acid resistance, especially, gastric acid resistance. The first natural water-soluble polymer is composed of one or at least two selected from the group consisting of gelatin, carrageenan, starch, agar, pullulan, modified starch, alginic acid and mannan, and the second natural water-soluble polymer is composed of one or at least two selected from the group consisting of pectin, gellan gum and curdlan.

Amount of the first natural water-soluble polymer falls within the range of 1 to 98% by mass, preferably 2 to 85% by mass, and more preferably 3 to 70% by mass, based on the total weight of the dried film. When the amount of the first natural water-soluble polymer is less than 1% by mass, strength of the formed capsule is low, and when it exceeds 98% by mass, functions of acid resistance and large intestine disintegration cannot be imparted.

Amount of the second natural water-soluble polymer falls within the range of 1 to 24% by mass, preferably 2 to 18% by mass, and more preferably 3 to 6% by mass, based on the total weight of the dried film. When the amount of the second natural water-soluble polymer is less than 1% by mass, the film of the formed capsule does not have sufficient acid resistance, and when it exceeds 24% by mass, the viscosity of the film solution becomes high, making it difficult to form a capsule.

The film of the capsule for treating ulcerative colitis of the present invention includes a film in which chitosan powder is dispersed in a film base material of a natural water-soluble polymer. Chitosan is obtained by deacetylating chitin, which is a polysaccharide in which N-acetyl-D-glucosamine units are linearly linked by β-1,4-bonds, by boiling treatment in concentrated alkali or the like, and the chitin is contained in a crust of a crab or a shrimp, an insect epidermis, skeleton of a squid or the like, and cell walls of fungi such as mushrooms. It is desirable that the chitosan powder used in the capsule of the present invention is of animal origin or plant origin, as described above.

The particle size of the chitosan powder used in the capsule of the present invention falls within the range of 90% or more passing through a sieve with an opening size of 22 μm (580 mesh) to 90% or more passing through a sieve with an opening size of 355 μm (42 mesh), preferably 90% or more passing through a sieve with an opening size of 45 μm (330 mesh) to 90% or more passing through a sieve with an opening size of 250 μm (60 mesh), and more preferably 90% or more passing through a sieve with an opening size of 75 μm (200 mesh) to 90% or more pass through a sieve with an opening size of 180 μm (83 mesh), according to sieve test standard JIS Z8801. When the particle size of the chitosan powder is smaller than 90% or more passing through a sieve with an opening size of 22 μm (580 mesh), the viscosity of the natural water-soluble polymer solution in which the chitosan powder is dispersed becomes high, making it difficult to form a capsule, and when it is larger than 90% or more passing through a sieve with an opening size of 355 μm (42 mesh), the chitosan powder is difficult to be uniformly dispersed in the film, making it difficult to form a capsule and not exhibiting a stable large intestine disintegrating function.

Amount of the chitosan powder falls within the range of 1 to 27% by mass, preferably 3 to 18% by mass, and more preferably 6 to 12% by mass, based on the total weight of the dried film. When the amount of the chitosan powder is less than 1% by mass, the large intestine disintegrating function cannot be exhibited due to the small amount of dispersed chitosan powder, and when it exceeds 27% by mass, the amount of dispersed chitosan powder is too large to form a capsule.

The film of the capsule for treating ulcerative colitis of the present invention may further contain a plasticizer in order to impart flexibility in a dry state, and examples of the plasticizer include glycerin, sorbitol, and the like. Amount of the plasticizer falls within the range of 1 to 50% by mass, preferably 5 to 40% by mass, and more preferably 15 to 30% by mass, based on the total weight of the dried film. When the amount of the plasticizer is less than 1% by mass, the film cannot withstand vacuum drying or may not maintain sufficient flexibility in a dry state to cause cracking, when it exceeds 50% by mass, the film softens and adhesion or melting occurs at high temperature.

Furthermore, the film of the capsule for treating ulcerative colitis of the present invention, in order to achieve large intestine-specific disintegration even when the hydrochloric acid concentration of the gastric juice is low due to anoxia or hypoacidity and the like, it is desirable that the film contains an organic acid, an inorganic acid, a pH adjuster, a compound containing divalent ions, or a combination thereof. The material such as the organic acid can be applied to the surface of the capsule, or the capsule immediately after formation can be put into a dipping solution containing the compound such as the organic acid to react.

In the capsule for treating ulcerative colitis of the present invention, in order to maintain or increase the therapeutic effect of indigo, an adherable substance to an epithelial of large intestine or a substance increasing residence time in the large intestine alone or in a mixture thereof can be also contained in any layer or layers of the capsule or applied to the surface of the capsule.

Further, in the capsule for treating ulcerative colitis of the present invention, in order to maintain or increase the therapeutic effect of indigo, the capsule can include a content which contains indigo powder coated with the adherable substance to the epithelial of large intestine. The capsule for treating ulcerative colitis of the present invention exerts a therapeutic effect by releasing the active ingredient indigo in the large intestine after reaching the large intestine and coming into contact with inflammatory cells. Therefore, in order to maintain or increase the therapeutic effect of indigo, it is also desired to extend the residence time in the large intestine by improving the intestinal epithelial adhesion of indigo.

The adherable substance to the epithelial of large intestine may be any substance that has a property of adhering to large intestine epithelium and is pharmaceutically acceptable, and examples thereof include fat-soluble tocopherol (vitamin E), mucus glycoprotein mucin, polysaccharides produced by microorganisms such as bifidobacteria, polyphosphoric acid, basic polymers such as polyvinylpyrrolidone (PVP), polymers such as xanthan gum, guar gum, tamarind seed gum, gum arabic, alginic acid, pregelatinized starch, carboxyvinyl polymer (Carbopol 974P NF commercially available from CBC Co., Ltd., Hiviswako 103 commercially available from Wako Pure Chemical Industries, Ltd.), poly-N-vinyl acetamide (PNVA), polyethylene glycol, polyvinyl alcohol, acrylic acid/acrylic acid octyl copolymer, silkfibroin acrylate copolymer resin, methacrylic acid/acrylic acid n-butyl copolymer, polyacrylic acid/acrylic acid octyl ester copolymer, acrylic acid-2-ethylhexyl/vinylpyrrolidone copolymer, methyl acrylate/acrylic acid-2-ethylhexyl copolymer resin, carmellose, hydroxyethyl cellulose, hydroxypropyl cellulose, methyl cellulose, carboxymethyl ethyl cellulose, sodium carboxymethyl starch, crystalline cellulose, cyclodextrin, polyisoprene, polyacrylic acid and sodium polyacrylate, rubbers, and the like. In addition, the substance increasing residence time in the intestine may be, similarly, any substance that has a long residence time in the intestine, especially in the large intestine, and is pharmaceutically acceptable, and examples thereof include dietary fibers such as indigestible dextrin. The most preferable adherable substance to the epithelial of large intestine is fat-soluble tocopherol (vitamin E), which is preferably contained in the content or protective layer. Amount of the substance falls within the range of 0.5 to 40% by mass of the whole capsule, and the coating amount falls within the range of 1 to 100% by mass of the whole capsule, and it is preferable that the coating amount is amount that does not impair formulation properties of the capsule, and that does not inhibit capsule disintegration in the large intestine. In addition, the method for coating the indigo powder with the adherable substance to the epithelial of large intestine is not particularly limited, and examples thereof include a fine particle coating method using a fluidized bed or the like. The amount of the adherable substance to the epithelial of large intestine, which is applied to the indigo powder, preferably falls within the range of 0.1 to 100% by mass of the whole indigo powder.

It is desirable that the dried film of the capsule of the present invention has a thickness of 10 to 600 µm, preferably 30 to 400 µm, and more preferably 40 to 250 µm. When the thickness of the film is less than 10 µm, film strength is low, and when the thickness is more than 600 µm, the amount of the content is small and disintegration is also poor.

In the production of the capsule for treating ulcerative colitis of the present invention, when a triple nozzle dropping method is used, it is preferable to discharge the content from an innermost nozzle, discharge the film from an outermost nozzle, and discharge an oily substance as the protective layer from an intermediate nozzle. In this case, the obtained capsule has a triple-layered structure, and an innermost portion of the capsule contains the content, thus infiltration of digestive juice or the like from the outside is very small, which is considered to be the most excellent embodiment.

The capsule for treating ulcerative colitis obtained as described above is subjected to ventilation drying at 5° C. to 30° C. for 2 to 12 hours. Further, vacuum drying or vacuum freeze drying may be further performed after ventilation drying. In vacuum drying, the degree of vacuum is maintained at 0.5 to 0.002 MPa or less, and further in vacuum freeze drying, it is frozen at −20° C. or less and dried. The time required for vacuum drying or vacuum freeze drying is not particularly limited, but is generally 5 to 60 hours, and preferably 24 to 48 hours. When it is less than 5 hours, the drying is insufficient, and water present in the capsule adversely affects the content.

The size of the capsule for treating ulcerative colitis of the present invention is not particularly limited, but it is desirable that the capsule has a diameter of 0.3 to 10 mm, and preferably 1 to 8 mm. When the diameter of the capsule is less than 0.3 mm, the thickness of the protective layer of the three-layer structure is reduced and the effect of preventing infiltration of water is reduced, and when the diameter is more than 8 mm, it is difficult to swallow.

The capsule for treating ulcerative colitis of the present invention is used for treating ulcerative colitis in humans and mammals. The capsule is preferably administered orally. A dose of the capsule of the present invention depends on the subject (human and mammal), age, individual difference, and medical condition, and for example, the daily dose for an adult (about 60 kg) is usually 0.05 to 120 mg/day, preferably 0.05 to 80 mg/day, more preferably 0.05 to 20 mg/day, and most preferably 0.50 to 15 mg/day, as the amount of indigo which is a drug for treating ulcerative colitis. Of course, the dose may be increased and decreased according to the medical condition. Also, the administration may be once a day or may be divided into multiple times.

The capsule for treating ulcerative colitis of the present invention has a film having large intestine-specific disintegration, but the disintegration mechanism is not a simple mechanism in which the outermost layer of the multi-layered capsule disintegrates in each environment, while proceeding to the stomach, small intestine and large intestine in order, after oral administration. In the capsule of the present invention, a natural water-soluble polymer is used as a film base material, in which chitosan powder is dispersed in a composite matrix of a gel of a first natural water-soluble polymer such as gelatin, carrageenan and starch that imparts particularly excellent mechanical strength and film-forming ability and adhesiveness to a capsule, and an acid-resistant gel of a second natural water-soluble polymer such as pectin that imparts acid resistance, particularly gastric acid resistance.

First, the pH is very low in the stomach due to gastric acid, and the first natural water-soluble polymer that does not have gastric acid resistance is partially eroded by gastric acid, but the content is protected by a film (preferably in combination with a protective layer) of the second natural water-soluble polymer that has gastric acid resistance. At the same time, the chitosan powder that was dispersed in the natural water-soluble polymer changes to sol (solution state) in the acid resistant film due to the acidic aqueous solution, but the content does not easily flow outside the capsule because there is chitosan sol dispersed in the acid resistant film. Then, the capsule for treating ulcerative colitis proceeds to the small intestine in such a state, but the pH rises in the small intestine and the acid resistant film disintegrates, and at the same time, the chitosan sol dispersed in the natural water-soluble polymer is gelled to form a chitosan film, and the content is protected by the chitosan film and the protective layer. Finally, in the large intestine, the chitosan film is specifically decomposed by organic acid and enzyme such as lysozyme produced by a large number of anaerobic microorganisms, and the protective layer of the capsule also disintegrates to release the content (that is, indigo which is an active ingredient for treating ulcerative colitis).

In the capsule for treating ulcerative colitis disintegrating in the large intestine of the present invention, indigo which is an active ingredient for treating ulcerative colitis that has been protected up to the large intestine is released in the large intestine to exert its medicinal effect. In addition, in order to maintain or increase the therapeutic effect of indigo, an adherable substance to an epithelial of large intestine or a substance increasing residence time in the large intestine alone or in a mixture thereof is added to any layer or layers of the capsule or applied to the surface of the capsule, or the capsule includes a content containing indigo powder coated with the adherable substance to the epithelial of large intestine, thereby greatly reducing ulcerative colitis.

EXAMPLES

The present invention will be described in more detail by way of examples. The present invention should not be construed as limited to these examples.

Preparation Example 1

Formation of Indigo-Containing Capsule A (a) Content liquid: a dispersion of 8.33 g of indigo (manufactured by Tokyo Chemical Industry Co., Ltd., purity 97%) in a melt of 91.67 g of an oily substance (glycerin fatty acid ester) with a melting point of 32° C. was prepared as a content liquid.

(b) Protective layer liquid: 90.00 g of glycerin fatty acid ester (melting point 42° C.), 7.00 g of lecithin and 3.00 g of fine silicon dioxide were mixed to obtain a protective layer liquid.

(c) Film liquid: 67.00 g of acid-treated gelatin derived from pig skin (jelly strength: 240 Bloom), 24.00 g of food additive concentrated glycerin, 3.00 g of low methoxyl (LM) pectin (DE value of esterification degree: 27) and 6.00 g of squid chitosan (acetylation degree: 80 or more; particle size: 90% or more passing through a sieve having an opening size of 250 μm (60 mesh), according to sieve test standard JIS Z8801) were mixed to obtain a film liquid.

A seamless capsule having a three-layered structure was formed by simultaneously dropping the content liquid from an inner nozzle of a concentric triple nozzle, the protective layer liquid from an intermediate nozzle outside thereof, and the film liquid from an outermost nozzle into a cooled and flowing oil. The obtained capsule was dried by aeration at 20° C. for 6 hours to prepare an indigo-containing capsule A having a three-layered structure. A diameter of the capsule A was 1.9 mm and a weight of the capsule A was 3.89 mg. An indigo content per the capsule A was 0.1 mg.

Creation of Colitis Mice

As mice used in an animal test, C57BL/6J was started to use after preliminary breeding for 3 days after purchase. First, a 2.0% solution of DSS (dextran sulfate sodium salt, molecular weight 36,000 to 44,000) was given to mice to cause colitis to prepare colitis model mice.

Control Mice

The colitis model mice were administered with only sterilized water to obtain control mice. It should be noted that, in order to maintain the colitis state of the mice for 7 days, the 2.0% DDS (dextran sulfate sodium salt) solution was orally administered at the same time as the administration of the sterile water.

Example 1

Five capsules (equivalent to indigo amount of 0.5 mg) and 15 capsules (equivalent to indigo amount of 1.5 mg) both of which were the indigo-containing capsules A were each orally administered to 5 specimens of colitis mice for 7 days. It should be noted that, in order to maintain the colitis state of the mice for 7 days, the 2.0% DDS (dextran sulfate sodium salt) solution was orally administered at the same time when the oral administration of the capsules A.

Evaluation Results

Colitis-suppressing action of indigo was evaluated by a decrease in the endpoints such as body weight (BW), disease activity index (DAI) score (DAI score: a total score (0 to 12) of the number of defecation, bloody stool, mucosal findings, and general endpoints scored 0 to 3 on a 4-point scale), and colon length. Since body weight loss, increase in disease activity index core, and shortening of the colon length were observed with progress of pathological condition of colitis, the intestines of the mice after administration were examined, and the presence or absence of colitis was determined by the above endpoints.

Figure 1:
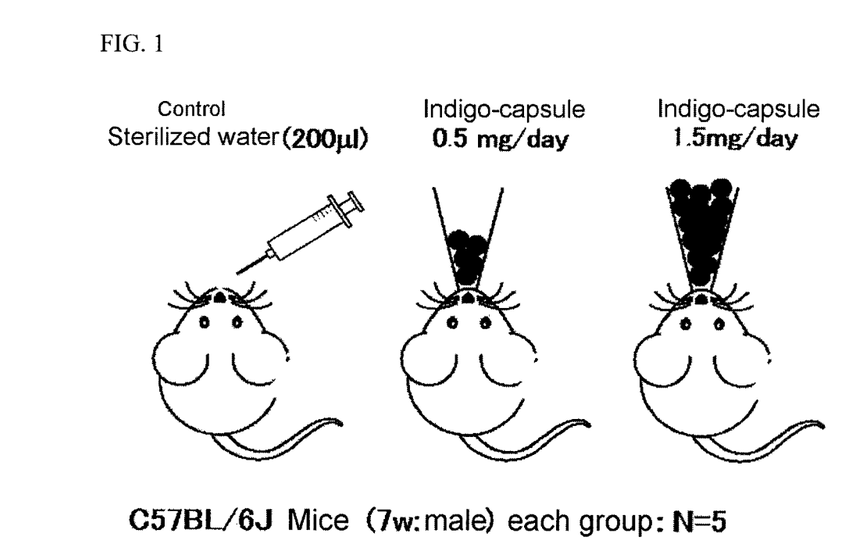
FIG. 1 is a pictorial representation of the types of mice used in the examples for easy understanding. The leftmost picture is a mouse administered with 200 μL of sterilized water as a control, the second from the left is a mouse administered with 5 indigo-containing capsules A per day (the amount of indigo is 0.5 mg/day), and the rightmost is a mouse administered with 15 indigo-containing capsules per day (the amount of indigo is 1.5 mg/day).
Figure 2:
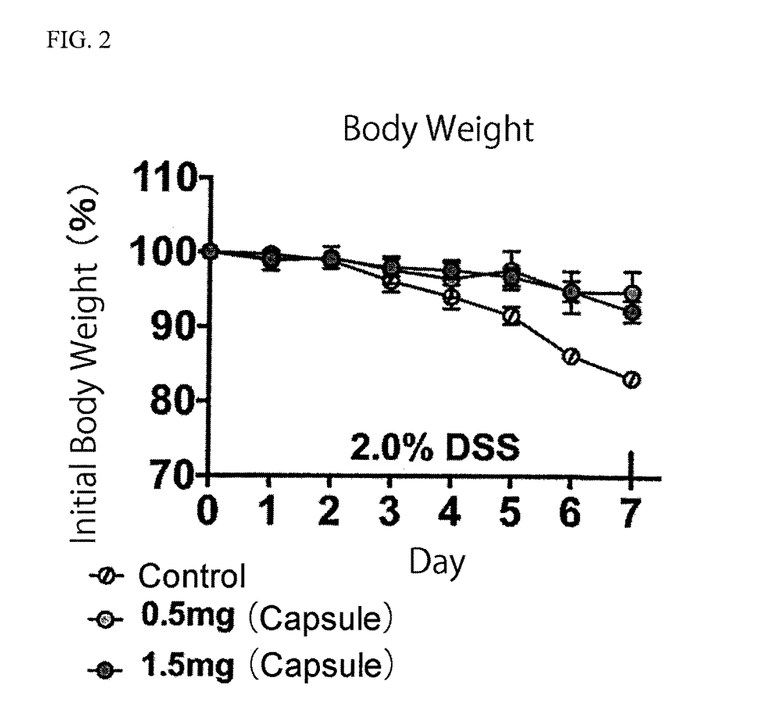
FIG. 2 is a graph representing changes in body weight (BW) of mice for 7 days.
Figure 3:
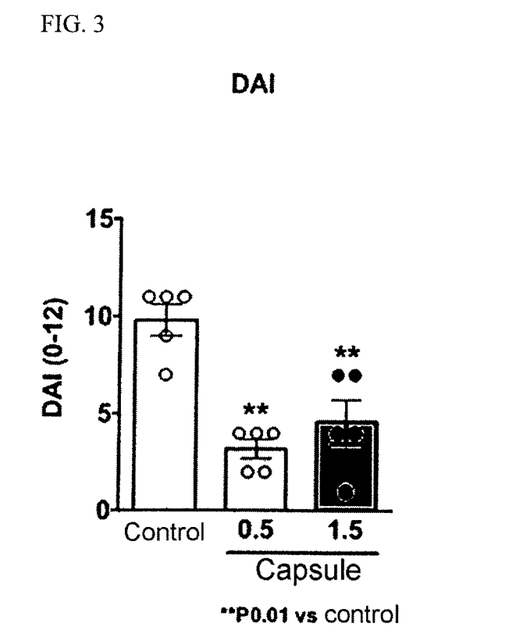
FIG. 3 is a graph representing results of disease activity index score (DAI score).
Figure 4:
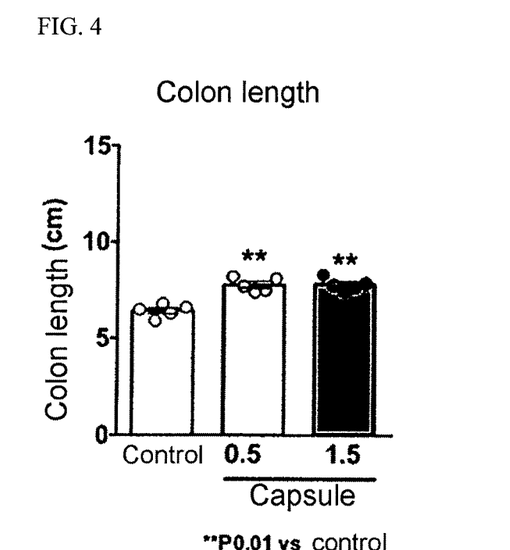
FIG. 4 is a graph representing results of measuring colon length.
Figure 5:
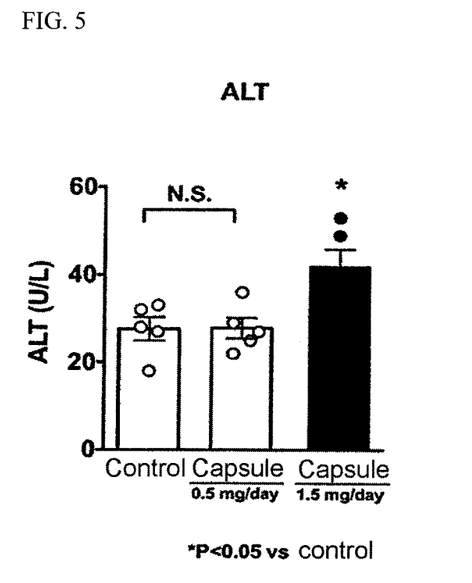
FIG. 5 is a graph representing indigo hepatotoxicity confirmed with serum ALT index.

The results of the evaluation measurements are represented in FIG. 2 to FIG. 4. It should be noted that FIG. 1 is a pictorial form of the types of mice used in the evaluation for easy understanding. FIG. 5 represents indigo hepatotoxicity confirmed with serum ALT index, which was measured in control and capsule-administered mice.

FIG. 1 is a pictorial form of the types of mice used in the evaluation for easy understanding, in which the left picture is a mouse administered with 200 μL of sterilized water as a control, the second from the left is a mouse administered with 5 indigo-containing capsules A per day (equivalent to indigo amount of 0.5 mg/day), and the rightmost is a mouse administered with 15 indigo-containing capsules A per day (equivalent to indigo amount of 1.5 mg/day).

FIG. 2 is a graph representing changes in body weight (BW) of mice for 7 days. The rate of change in the average body weight of the mice of each embodiment is described, with the average value of the body weight at the start of the experiment being 100%. As is clear from FIG. 2, the indigo-containing capsule administration groups (5 tablets (equivalent to indigo amount of 0.5 mg/day) and 15 tablets (equivalent to indigo amount of 1.5 mg/day)) showed less body weight loss, and the pathological condition of colitis was clearly mild.

FIG. 3 is a graph representing results of disease activity index score (DAI score). It should be noted that the DAI score refers to an evaluation index described in the literature "Sutherland L R, Martin F, Greer S, et al: 5-Aminosalicylic acid enema in the treatment of distal colitis, proctosigmoiditis, and proctitis. Gastroenterology 92: 1894-1898, 1987".

As is clear from FIG. 3, the pathological condition of colitis in the groups administrated 5 indigo-containing capsules A (equivalent to indigo amount of 0.5 mg/day) and 15 indigo-containing capsules A (equivalent to indigo amount of 1.5 mg/day) were significantly alleviated in both low and high doses than that in the control group. Based on the above, it could be confirmed that the indigo-containing capsule A administration groups suppressed colitis with a lower dose of indigo.

FIG. 4 is a graph representing results of measuring colon length. Since the colon length is shortened by causing colitis, the colon length of each mouse group was measured as another index for the evaluation of colitis, and the average value thereof was represented by a histogram.

As shown in FIG. 4, the indigo-containing capsule administration groups (equivalent to indigo amounts of 0.5 mg and 1.5 mg/day) showed a significantly longer colon length than the control group. Based on this, it could be confirmed that the indigo-containing capsule administration groups suppressed colitis even at a lower concentration of indigo amount.

Regarding the mice that were orally administered with indigo powder as it was (equivalent to indigo amount of 0.5 mg/day) for 7 days, the results are not represented in FIGS. 2 to 4. However, as a result of the experiment, decreasing the body weight was also observed as compared with the control group, and the colon length was also the same as that of the control group, thus no effect of indigo was observed.

FIG. 5 is a graph representing indigo hepatotoxicity confirmed with serum ALT index. The serum ALT index was measured by ultraviolet absorptiometry described in JSCC (Japan Society of Clinical Chemistry) standardization method.

There was no difference between indigo-containing capsule A and indigo powder when evaluated using the ALT level as an endpoint. However, at 0.5 mg/day, where the indigo-containing capsule A showed a strong effect and the powder showed no effect, the indigo-containing capsule A had an ALT level equivalent to that of the control.

Based on these results, it was revealed that oral administration of 0.5 mg/day of indigo-containing capsule A can suppress the pathogenesis and progression of colitis in a mouse model of colitis without causing liver dysfunction. In other words, it was found that indigo-containing capsule A could provide a therapeutic window without indigo being contacted and absorbed in the small intestine.

Since the capsule of the present invention showed an effect at a low dose (equivalent to 25 mg/kg/day) showing no effect in powder administration even when compared with the low dose (60 mg/kg/day) of indigo powder described as effective in Non Patent Literature 4 in colitis model mice, it was shown to be a therapeutic agent for ulcerative colitis at a lower dose than administration by powder, and has little fear of side effects. Therefore, it can be provided as a drug that has little burden on the patient and little fear of side effects.

Example 2

In order to cope with high pH due to hypoxia, the indigo-containing capsule A of Preparation Example 1 was acid-treated in advance and re-dried to create a capsule, and a disintegration test was performed.

A capsule containing indigo that had been immersed in an acidic solution for 3 minutes or more was prepared, and immersed at pH 4.0, which is the pH assumed in the stomach of a mouse, at 37° C. for 60 minutes to perform a disintegration test. After 60 minutes, the capsule was taken out into a petri dish and photographed to confirm the state of the capsule. No disintegration of the capsule and no outflow of indigo in the capsule were observed.

Example 3

The following indigo-containing capsule B was formed in the same manner as the formation of the indigo-containing capsule A of Preparation Example 1.

(a) Content liquid: a dispersion of 8.33 g of indigo (manufactured by Tokyo Chemical Industry Co., Ltd., purity 97%) in a melt of 85.67 g of an oily substance (glycerin fatty acid ester) with a melting point of 32° C., 3.00 of lecithin and 3.00 of tocopherol was taken as a content liquid.

(b) Protective layer liquid: same as the one in the indigo-containing capsule A.

(c) Film liquid: same as the one in the indigo-containing capsule A.

In order to confirm improvement in adhesion to the large intestine, an in vitro test was performed using the following two types of plates assuming large intestine cells (both manufactured by Corning International K.K.).

(1) BioCoat™ Fibronectin 6 well plate (coating component: fibronectin)

(2) BioCoat™ Poly-D-Lysine/Laminin 6 well plate (coating component: poly-D-lysine/laminin)

The indigo-containing capsule A and the indigo-containing capsule B were each immersed in purified water at 10° C. for 5 minutes, so that the film was swelled and then peeled off and removed, and they were added to and dissolved in a digestive enzyme solution (Japanese Pharmacopoeia Disintegration Test Solution II added with pancreatin, yatalase and a surfactant), and the dissolved liquids were designated as capsule A at the time of large intestine disintegration and capsule B at the time of large intestine disintegration (prescription for studying improvement in adhesion to the large intestine), respectively.

The capsule form A at the time of large intestine disintegration and the capsule B at the time of large intestine disintegration (prescription for studying improvement in adhesion to the large intestine) were each placed on the above-mentioned two types of plates assuming large intestine cells and dissolved in an incubator at 37° C. After stirring at 500 rpm for 1 hour, the Japanese Pharmacopoeia Disintegration Test Solution II was added thereto, and unattached indigo was removed. Next, dimethyl sulfoxide (DMSO) was added thereto, the mixture was further stirred for 10 minutes, and DMSO obtained by dissolving and extracting indigo adhering to the plates assuming large intestine cells was each collected as sample solutions.

The adhesion rate of these sample solutions was determined by quantification using liquid chromatography (HPLC). Based on these results, more significant improvement in adhesion of indigo to the large intestine epithelial cells was confirmed in the capsule B which is a drug obtained by adding tocopherol to the content liquid of the capsule than the capsule A.

INDUSTRIAL APPLICABILITY

The present invention is directed to a capsule for treating ulcerative colitis. The capsule is a capsule that does not easily disintegrate in the stomach and small intestine when delivered orally, and is delivered to the large intestine and disintegrates to exert its effect. The present invention suppresses onset of pulmonary arterial hypertension, which is a serious side effect, and greatly contributes to treatment of ulcerative colitis that is intractable and extremely bad for quality of life (QOL), by "reduction of the amount of indigo to be administered" and "specific delivery of indigo to the large intestine". Further, in order to maintain or increase the therapeutic effect of indigo, an adherable substance to an epithelial of large intestine or a substance increasing residence time in the large intestine alone or in a mixture thereof is blended in any layer or layers of the capsule or applied to the surface of the capsule, or the capsule includes a content containing indigo powder coated with the adherable substance to the large intestine epithelial, thereby greatly reducing ulcerative colitis.

The invention claimed is:

1. A method for treating ulcerative colitis, comprising
orally administering to a subject a capsule that comprises indigo and a substance adherable to the epithelium of the large intestine, and
adhering indigo, in an amount effective for treating ulcerative colitis, to an epithelium of a large intestine of the subject in the presence of the substance adherable to the epithelium of the large intestine, wherein
the substance adherable to the epithelium of the large intestine is fat-soluble tocopherol,
an amount of the fat-soluble tocopherol falls within the range of 0.5 to 40% by mass of the whole capsule, and
the indigo acts as an active agent for the treating of the ulcerative colitis.

2. The method according to claim 1, wherein the capsule comprises an indigo-containing content, a protective layer coating the indigo-containing content and a film formed outside the protective layer,
wherein the indigo-containing content, the protective layer and the film are arranged concentrically in this order from inside to outside,
the protective layer comprises an oily substance,
the film comprises chitosan powder dispersed in a film base material of a natural water-soluble polymer, and
at least one selected from the group consisting of the content, the protective layer and the film contains the substance adherable to the epithelium of the large intestine.

3. The method according to claim 2, wherein the natural water-soluble polymer is a mixture of a first natural water-soluble polymer and a second natural water-soluble polymer, the first natural water-soluble polymer is composed of one or a mixture of at least two selected from the group consisting of gelatin, carrageenan, starch, agar, pullulan, modified starch, alginic acid, and mannan, and the second natural water-soluble polymer is composed of one or a mixture of at least two selected from the group consisting of pectin, gellan gum, and curdlan.

4. The method according to claim 2, wherein the capsule releases the indigo locally in the large intestine.

5. The method according to claim 2, wherein the film comprises a plasticizer.

6. The method according to claim 3, wherein the chitosan powder is of animal origin, and an amount of the chitosan powder falls within the range of 1 to 27% by mass, and an amount of the second natural water-soluble polymer falls within the range of 1 to 24% by mass, based on the total weight of the dried film.

7. The method according to claim 3, wherein the chitosan powder is of plant origin, and an amount of the chitosan powder falls within the range of 1 to 27% by mass, and an amount of the second natural water-soluble polymer falls within the range of 1 to 24% by mass, based on the total weight of the dried film.

8. The method according to claim 2, wherein the film base material of the natural water-soluble polymer is a mixture of gelatin and pectin.

9. The method according to claim 2, wherein the capsule has been treated with an acidic solution prior to the oral administration.

10. The method according to claim 2, wherein the indigo-containing content of the capsule comprises indigo powder and the substance adherable to the epithelium of the large intestine, the indigo powder being blended or coated with the substance adherable to the epithelium of the large intestine.

11. The method according to claim 2, wherein the capsule is administered to provide an amount of indigo of 0.05 to 120 mg/day, based on a 60 kg adult.

12. The method according to claim 2, wherein the capsule is administered to provide an amount of indigo of 0.05 to 20 mg/day, based on a 60 kg adult.

* * * * *

UNITED STATES PATENT AND TRADEMARK OFFICE
CERTIFICATE OF CORRECTION

PATENT NO. : 12,357,579 B2
APPLICATION NO. : 18/310999
DATED : July 15, 2025
INVENTOR(S) : Kanai et al.

It is certified that error appears in the above-identified patent and that said Letters Patent is hereby corrected as shown below:

On the Title Page

Item (71) Applicants: delete "KEIO UNIVERSITY, Tokyo (JP);" and insert --KEIO UNIVERSITY, Minato-ku, Tokyo (JP);--.

Item (71) Applicants: delete "Innovation at Kobe, Kobe (JP);" and insert --Innovation at Kobe, Kobe-shi, Hyogo (JP);--.

Item (71) Applicants: delete "JINTAN CO., LTD., Osaka (JP);" and insert --JINTAN CO., LTD., Osaka-shi, Osaka (JP);--.

Item (72) Inventors: delete "Takanori Kanai, Tokyo (JP);" and insert --Takanori Kanai, Shinjuku-ku; Tokyo (JP);--.

Item (72) Inventors: delete "Hideo Nishimura, Kobe (JP);" and insert --Hideo Nishimura, Kobe-shi, Hyogo (JP);--.

Item (72) Inventors: delete "Tomoyuki Koyama, Hirakata (JP);" and insert --Tomoyuki Koyama, Hirakata-shi, Osaka (JP);--.

Item (72) Inventors: delete "Takuhiko Adachi, Hirakata (JP);" and insert --Takuhiko Adachi, Hirakata-shi, Osaka (JP);--.

Item (72) Inventors: delete "Hiroyuki Hayakawa, Hirakata (JP);" and insert --Hiroyuki Hayakawa, Hirakata-shi, Osaka (JP);--.

Signed and Sealed this
Twenty-sixth Day of August, 2025

Coke Morgan Stewart
*Acting Director of the United States Patent and Trademark Office*